(12) United States Patent
Houze et al.

(10) Patent No.: US 10,472,609 B2
(45) Date of Patent: Nov. 12, 2019

(54) PROGENITOR CELLS OF MESODERMAL LINEAGE

(75) Inventors: Thomas Averell Houze, Boras (SE); Martin John Evans, Cardiff (GB); Ajan Reginald, Warwickshire (GB); Ina Laura Pieper, Swansea (GB)

(73) Assignee: Cell Therapy Limited, Singleton Park, Swansea (GB)

( * ) Notice: Subject to any disclaimer, the term of this patent is extended or adjusted under 35 U.S.C. 154(b) by 97 days.

(21) Appl. No.: 14/130,840

(22) PCT Filed: Jul. 6, 2012

(86) PCT No.: PCT/GB2012/051600
§ 371 (c)(1),
(2), (4) Date: Sep. 25, 2014

(87) PCT Pub. No.: WO2013/005053
PCT Pub. Date: Jan. 10, 2013

(65) Prior Publication Data
US 2015/0071886 A1    Mar. 12, 2015

(30) Foreign Application Priority Data

| Jul. 6, 2011 | (GB) | 1111500.3 |
| Jul. 6, 2011 | (GB) | 1111503.7 |
| Jul. 6, 2011 | (GB) | 1111505.2 |
| Jul. 6, 2011 | (GB) | 1111509.4 |

(51) Int. Cl.
*C12N 5/0775* (2010.01)
*A61K 35/28* (2015.01)
*A61K 35/12* (2015.01)

(52) U.S. Cl.
CPC ............ *C12N 5/0665* (2013.01); *A61K 35/28* (2013.01); *A61K 2035/124* (2013.01); *C12N 2500/02* (2013.01); *C12N 2502/115* (2013.01); *C12N 2506/115* (2013.01)

(58) Field of Classification Search
None
See application file for complete search history.

(56) References Cited

U.S. PATENT DOCUMENTS

| 2011/0123498 A1 | 5/2011 | Westenfelder |
| 2011/0293576 A1 | 12/2011 | Lange et al. |
| 2012/0276067 A1 | 11/2012 | Westenfelder |
| 2012/0288480 A1 | 11/2012 | Ho |
| 2013/0273011 A1 | 10/2013 | Ichim et al. |

FOREIGN PATENT DOCUMENTS

| CN | 102048756 A | 5/2011 |
| EP | 1845154 A1 | 10/2007 |
| EP | 2014294 A1 | 1/2009 |
| EP | 2205724 A1 | 7/2010 |
| RU | 2138162 C1 | 9/1999 |
| WO | 1999001145 A1 | 1/1999 |
| WO | 1999011287 A1 | 3/1999 |
| WO | 1999061587 A1 | 12/1999 |
| WO | 2001011011 A2 | 2/2001 |
| WO | 2003016916 A1 | 2/2003 |
| WO | 2003070922 A1 | 8/2003 |
| WO | 2004085630 A1 | 10/2004 |
| WO | 2005045011 A1 | 5/2005 |
| WO | 2006012404 A2 | 2/2006 |
| WO | 2006032075 A1 | 3/2006 |
| WO | 2006032092 A1 | 3/2006 |
| WO | 2006108229 A1 | 10/2006 |
| WO | 2007058404 A1 | 5/2007 |
| WO | 2007065927 A1 | 6/2007 |
| WO | 2007087139 A2 | 8/2007 |
| WO | 2008006168 A1 | 1/2008 |
| WO | 2008026226 A2 | 3/2008 |
| WO | 2008097828 A2 | 8/2008 |
| WO | 2008129563 A2 | 10/2008 |
| WO | 2008148105 A1 | 12/2008 |
| WO | 2009044943 A1 | 4/2009 |
| WO | 2009069991 A2 | 6/2009 |
| WO | 2009140452 A2 | 11/2009 |
| WO | 2010005527 A1 | 1/2010 |
| WO | 2010019997 A1 | 2/2010 |
| WO | 2010021412 A1 | 2/2010 |
| WO | 2010/033605 A2 | 3/2010 |
| WO | 2010052192 A1 | 5/2010 |
| WO | 2010057260 A1 | 5/2010 |
| WO | 2010126194 A1 | 11/2010 |
| WO | 2011048253 A1 | 4/2011 |
| WO | 2011068792 A2 | 6/2011 |
| WO | 2012000064 A1 | 1/2012 |
| WO | 2012027740 A1 | 3/2012 |
| WO | 2012048093 A2 | 4/2012 |

(Continued)

OTHER PUBLICATIONS

Zuckerman et al., Long-term human peripheral blood monocyte cultures: establishment, metabolism and morphology of primary human monocyte-macrophage cell cultures, Immunology, 1979, vol. 38, pp. 401-411.*

Hemeda et al., "Interferon-? and Tumor Necrosis Factor-? Differentially Affect Cytokine Expression and Migration Properties of Mesenchymal Stem Cells", Stem Cells and Development, 2010; 19(5): 693-706.

Bernardo et al., "Mesenchymal Stromal Cells A Novel Treatment Modality for Tissue Repair", Ann. N. Y. Acad. Sci., 2009; 1176: 101-117.

Abdallah et al., "The Use of Mesenchymal (Skeletal) Stem Cells for Treatment of Degenerative Diseases: Current Status and Future Perspectives", Cell. Physiol., 2009; 218: 9-12.

Buhring et al., "Novel Markers for the Prospective Isolation of Human MSC", Ann. N.Y. Acad. Sci., 2007; 1006:262-271.

(Continued)

*Primary Examiner* — Thomas J. Visone
*Assistant Examiner* — Evelyn Y Pyla
(74) *Attorney, Agent, or Firm* — Norton Rose Fulbright US LLP

(57) ABSTRACT

The invention relates to progenitor cells of mesodermal lineage and their use in therapy.

24 Claims, 4 Drawing Sheets

(56) References Cited

FOREIGN PATENT DOCUMENTS

| WO | 2012076741 | A1 | | 6/2012 | |
|---|---|---|---|---|---|
| WO | 2012155209 | A1 | | 11/2012 | |
| WO | 2012162754 | A1 | | 12/2012 | |
| WO | 2012162758 | A1 | | 12/2012 | |
| WO | 2013003899 | A1 | | 1/2013 | |
| WO | 2013033777 | A1 | | 1/2013 | |
| WO | WO 2013/121426 | | * | 2/2013 | ........... C12N 5/0775 |
| WO | 2013121426 | A1 | | 8/2013 | |
| WO | 2013151725 | A1 | | 10/2013 | |

OTHER PUBLICATIONS

Wu et al., "The Role of Chemokines in Mesenchymal Stem Cell Homing to Myocardium", Stem Cell Rev and Rep, 2012: 8: 243-250.

Ponte et al., "The In Vitro Migration Capacity of Human Bone Marrow Mesenchymal Stem Cells: Comparison of Chemokine and Growth Factor Chemotactic Activities", Stem Cells, 2007; 25: 1737-1745.

Chamberlain et al., "Murine Mesenchymal Stem Cells Exhibit a Restricted Repertoire of Functional Chemokine Receptors: Comparison with Human", PLoS ONE, 2008; 3 (8): e2934.

Kolf et al., "Mesenchymal stromal cells, Biology of adult mesenchymal stem cells: regulation of niche, self-renewal and differentiation", Arthritis Research & Therapy, 2007; 9: 204.

Kia et al., "Comparative Analysis of Chemokine Receptor's Expression in Mesenchymal Stem Cells Derived from Human Bone Marrow and Adipose Tissue", Mol Neurosci, 2011; 44: 178-185.

Quan-Hua et al., "Are CD133 and CD271 useful in positive selection to enrich umbilical cord blood mesenchymal stem cells?", Journal of Experimental Hematology, 2010; 18(5): 1286-1291.

Abdallah et al., "Human mesenchymal stem cells: from basic biology to clinical applications", Gene Therapy, 2008; 15: 109-116.

Jarocha et al., "Advantage of mesenchymal stem cells (MSC) expansion directly from purified bone marrow CD105+ and CD271+ cells", Folia Histochem Cytobiol., 2008; 46 (3): 307-314.

Castilho-Fernandes et al., "Human hepatic stellate cell line (LX-2) exhibits characteristics of bone marrow-derived mesenchymal stem cells", Experimental and Molecular Patholgy, 2011; 91: 664-672.

Carrancio et al., "Optimization of mesenchymal stem cell expansion procedures by cell separation and culture conditions modification", Experimental Hematology, 2008; 36: 1014-1021.

Holzwarth et al., "Low physiologic oxygen tensions reduce proliferation and differentiation of human multipotent mesenchymal stromal cells", BMC Cell Biology, 2010; 11: 11.

Lui et al., "Hypoxic preconditioning advances CXCR4 and CXCR7 expression by activating HIF-1a in MSCs", Biochemical and Biophysical Research Communications, 2010; 401: 509-515.

Wagner et al., "Mesenchymal Stem Cell Preparations—Comparing Apples and Oranges", Stem Cell, 2007; 3: 239-248.

Wagner et al, "Comparative characteristics of mesenchymal stem cells from human bone marrow, adipose tissue, and umbilical cord blood", Experimental Hemotology, 2205; 33: 1402-1416.

Simmons et al., "Identification of stromal cell precursors in human bone marrow by a novel monoclonal antibody, STRO-1", Blood, 1991; 78: 55-62.

Quirici et al., "Isolation of bone marrow mesenchymal stem cells by anti-nerve growth factor receptor antibodies", Experimental Hemotology, 2002; 30: 783-791.

Reyes et al., "Purification and ex vivo expansion of postnatal human marrow mesodermal progenitor cells", Blood, 2001; 98: 2615-2625.

Gottschling et al., "Human Mesenchymal Stromal Cells Regulate Initial Self-Renewing Divisions of Hematopoietic Progenitor Cells by a β1-Integrin-Dependent Mechanism", Stem Cells, 2007; 25: 798-806.

Gronthos et al., "Molecular and cellular characterisation of highly purified stromal stem cells derived from human bone marrow", Journal of Cell Science, 2003; 116: 1827-1835.

Miura et al., "Defective osteogenesis of the stromal stem cells predisposes CD18-null mice to osteoporosis", PNAS, 2005; 102 (39); 14022-14027.

Gang et al, "SSEA-4 identifies mesenchymal stem cells from bone marrow," Blood, 2007; 109: 1743-1751.

Honczarenko et al., "Human Bone Marrow Stromal Cells Express a Distinct Set of Biologically Functional Chemokine Receptors," Stem Cells, 2006; 24: 1030-1041.

Zuk et al., "Human Adipose Tissue Is a Source of Multipotent Stem Cells", Molecular Biology of the Cell, 2002; 13: 4279-4295.

Da Silva Meirellas et al., "Mesenchymal stem cells reside in virtually all post-natal organs and tissues", J Cell Sci, 2006; 119: 2204-2213.

Tuli et al., "Characterization of Multipotential Mesenchymal Progenitor Cells Derived from Human Trabecular Bone", Stems Cells, 2003; 21: 681-693.

Colter et al., "Identification of a subpopulation of rapidly selfrenewing and multipotential adult stem cells in colonies of human marrow stromal cells", PNAS, 2001; 98(14): 7841-7845.

Haynesworth et al., "Cell Surface Antigens on Human Marrow-Derived Mesenchymal Cells Are Detected by Monoclonal Antibodies", Bone, 1992; 13:69-80.

Etheridge et al., "Expression Profiling and Functional Analysis of Wnt Signaling Mechanisms in Mesenchymal Stem Cells", Stem Cells, 2004; 22: 849-860.

Gronthos et al, "Surface Protein Characterization of Human Adipose Tissue-Derived Stromal Cells", Journal of Cellular Physiology, 2001; 189: 54-63.

Baddoo et al., "Characterization of Mesenchymal Stem Cells Isolated From Murine Bone Marrow by Negative Selection", Journal of Cellular Biochemistry, 2003; 89: 1235-1249.

Peister et al., "Adult stem cells from bone marrow (MSCs) isolated from different strains of inbred mice vary in surface epitopes, rates of proliferation, and differentiation potential", Blood, 2004; 103: 1662-1668.

Da Silva Meirellas et al., "Murine marrow-derived mesenchymal stem cell: isolation, in vitro expansion, and characterization", British Journal of Haematology, 2003; 123: 702-711.

Sakaguchi et al., "Comparison of Human Stem Cells Derived From Various Mesenchymal Tissues", Arthritis & Rheumatism, 2005; 52(8): 2521-2529.

Ip et al.,"Mesenchymal Stem Cells Use Integrin β1 Not CXC Chemokine Receptor 4 for Myocardial Migration and Engraftment", Molecular Biology of the Cel, 2007; 18: 2873-2882.

Simmons and Torok-Storb, "Identification of Stromal Cell Precursors in Human Bone Marrow by a Novel Monoclonal Antibody, STRO-1", Blood, vol. 78, No. 1 (Jul. I), 1991: pp. 55-62.

Herrera et al., "Exogenous mesenchymal stem cells localize to the kidney by means of CD44 following acute tubular injury", Kidney International, 2007; 72: 430-441.

Viswanathan et al., "Functional Expression of N-Formyl Peptide Receptors in Human Bone Marrow-Derived Mesenchymal Stem Cells", Stem Cells, 2007; 25: 1263-1269.

Brooke et al., "Molecular Trafficking Mechanisms of Multipotent Mesenchymal Stem Cells Derived from Human Bone Marrow and Placenta", Stem Cells and Development, 2008; 17: 929-940.

Sordi et al., "Bone marrow mesenchymal stem cells express a restricted set of functionally active chemokine receptors capable of promoting migration to pancreatic islets", Blood, 2005; 106: 419-427.

Huang et al., "Genetic Modification of Mesenchymal Stem Cells Overexpressing CCR1 Increases Cell Viability, Migration, Engraftment and Capillary Density in the Injured Myocardium", Circ Res., 2010; 106(11): 1753-1762.

Ringe et al., "Towards In Situ Tissue Repair: Human Mesenchymal Stem Cells Express Chemokine Receptors CXCR1, CXCR2 and CCR2, and Migrate Upon Stimulation With CXCL8 but not CCL2", Journal of Cellular Biochemistry, 2007; 101: 135-146.

Luttichau et al., "Human Adult CD34 Progenitor Cells Functionally Express the Chemokine Receptors CCR1, CCR4, CCR7, CXCR5, and CCR10 but Not CXCR4", Stem Cells and Development, 2205; 14: 329-336.

(56) References Cited

OTHER PUBLICATIONS

Le Blanc et al., "HLA expression and immunologic properties of differentiated and undifferentiated mesenchymal stem cells", Experimental Hematology, 2003; 31: 890-896.

Anker et al., "Mesenchymal stem cells in human second-trimester bone marrow, liver, lung, and spleen exhibit a similar immunophenotype but a heterogeneous multilineage differentiation potential", Haematologica, 2003; 88: 845-852.

Pittenger et al., "Multilineage Potential of Adult Human Mesenchymal Stem Cells", Science, 1999; 284: 143.

Kucia et al., "A population of very small embryonic-like (VSEL) CXCR4+ SSEA-1+ Oct-4+ stem cells identified in adult bone marrow", Leukemia, 2006; 20: 847-869.

Anjos-Afonso et al., "Nonhematopoietic/endothelial SSEA-1+ cells define the most primitive progenitors in the adult murine bone marrow mesenchymal compartment", Blood, 2007; 109: 1298-1306.

Battula et al., "Isolation of functionally distinct mesenchymal stem cell subsets using antibodies against CD56, CD271, and mesenchymal stem cell antigen-1", Haematologica, 2009; 94(2): 173-174.

Sagi et al., "Positional Identity of Murine Mesenchymal Stem Cells Resident in Different Organs Is Determined in the Postsegmentation Mesoderm", Stem Cells and Development, 2012; 21(5): 814-828.

Zaim et al., "Donor age and long-term culture affect differentiation and proliferation of human bone marrow mesenchymal stem cells", Ann Hemato, 2012; 91(8): 1175-1186.

Capelli et al., "Human platelet lysate allows expansion and clinical grade production of mesenchymal stromal cells from small samples of bone marrow aspirates or marrow filter washouts", Bone Marrow Transplatation, 2007; 40: 785-791.

Granero-Molto et al., "Regenerative Effects of Transplanted Mesenchymal Stem Cells in Fracture Healing", Stem Cells, 2009; 27: 1887-1898.

Chinese Office Action dated Jan. 25, 2016 entered during prosecution of related Chinese Application No. 201280033446.3.

Arnhold et al. "Transplantation of bone marrow-derived mesenchymal stem cells rescue photoreceptor cells in the dystrophic retina of the rhodopsin knockout mouse", Graefe's Arch Clin Exp Ophthalmol (2007) 245:414-422.

Pilling et al., "Identification of Markers that Distinguish Monocyte-Derived Fibrocytes from Monocytes, Macrophages, and Fibroblasts", PLoS One, Oct. 2009, vol. 4, Issue 10, pp. 1-18.

Jersmann et al., "Time to abandon dogma: CD14 is expressed by non-myeloid lineage cells", Immunology and Cell Biology (2005) 83, pp. 462-467.

Altin and Sloan, "The role of CD45 and CD45-associated molecules in T cell activation", Immunology and Cell Biology (1997), 75, pp. 430-445.

Ohnishi, Shunsuke et al; Effect of Hypoxia on Gene Expression of Bone Marrow-Derived Mesenchymal Stem Cells and Mononuclear Cells; Stem Cell Genetics and Genomics 2007; 25:1116-1177.

Zhu, Ling-Ling, et al; Gene Expression Profiles and Metabolic Changes in Embryonic Neural Progenitor Cells Under Low Oxygen; Cellular Reprogramming; vol. 13, No. 2, pp. 113-121; 2011.

Park, Jong Kuk et al; ICAM-3 Enhances the Migratory and INvasive Potential of Human Non-Small Cell Lung Cancer Cells by inducing MMP-2 and MMP-9 via Akt and CREB; International Journal of Onocology; 36: 181-192; 2010.

Arbones, Maria L. et al; Lymphocyte Homing and Leukocyte Rolling and Migration are Impaired in L-Selectin-Deficient Mice; Immunitiy, vol. 1, 247-260; Jul. 1994.

Briaud, Stephanie A. et al; Leukocyte Trafficking and Myocardial Reperfusion Injury in ICAM-1/P-Selectin-Knockout Mice; Am. J. Physiol Heartl Circ. Physiol 280; H60-H67; 2001.

Huang, Miao-Tzu et al; Endothelial Intercellular Adhesion Modecule (ICAM)-2 Regulates Angiogensis; BloodJournal.org; vo. 106, No. 5; Sep. 2005.

Oberg, Hans-Heinrich et al; Differential Expression of CD126 and CD130 mediates different STAT-3 Physphorylation in CD4+CD25- and CD25high Regulatory T Cells; International immunology, vol. 18, No. 4; pp. 555-563.

Lonza; Mesenchymal Stem Cells; <http://www.lonza.com/products-services/bio-research/stem-cells/adult-stem-cells-and-media/human-mesenchymal-stem-cells-media/hmsc-human-mesenchymal-stem-cells.aspx>.

Ina Laura Pieper; PML patent Inventorship Letter of May 29, 2014 re Date PML Patent was filed in Great Britain: Jun. 6, 2011.

Japanese Notification of Reasons for Rejection dated Oct. 29, 2018 during prosecution of related JP Appl. No. 2014-517958.

Eurasian Search Report dated Jun. 21, 2018 during prosecution of related Eurasian Patent Application No. 201792475/26.

* cited by examiner

PROGENITOR CELLS OF MESODERMAL LINEAGE

This Application claims priority to PCT Patent Application Serial No. PCT/GB2012/051600, filed on Jul. 6, 2012, which claims priority to GB Application Serial Nos. 1111500.3; 1111503.7; 1111505.2; and 1111509.4 previously filed on Jul. 6, 2011, all of which are incorporated by reference herein in their entirety.

FIELD OF THE INVENTION

The invention relates to progenitor cells of mesodermal lineage and their use in therapy.

BACKGROUND TO THE INVENTION

Mesenchymal stem cells (MSCs) are multipotent, adult stem cells. MSCs differentiate to form the different specialised cells found in the skeletal tissues. For example, they can differentiate into cartilage cells (chondrocytes), bone cells (osteoblasts) and fat cells (adipocytes).

MSCs are used in a variety of therapies, such as the treatment of Age-related Macular Degeneration (AMD) and myocardial infarct. Once administered to the patient, the MSCs typically migrate (or home) to the damaged tissue and exert their therapeutic effects through paracrine signaling and by promoting survival, repair and regeneration of the neighbouring cells in the damaged tissue.

Current therapies typically involve the infusion of a mixture of MSC subtypes some of which do not migrate efficiently to the tissue of interest. This necessitates the use of a high cell-dose which can lead to off-target side effects and volume-related side effects. MSCs are typically obtained from bone marrow and so it is difficult to obtain large amounts.

SUMMARY OF THE INVENTION

The inventors have surprisingly identified a new class of progenitor cells of mesodermal lineage (PMLs) having a specific marker expression pattern. Homogenous populations of the PMLs of the invention can be isolated from mononuclear cells (MCs), such as peripheral blood MCs. The PMLs are capable of efficiently migrating to and repairing damaged tissues.

The invention provides a progenitor cell of mesodermal lineage, wherein the cell (a) expresses detectable levels of CD29, CD44, CD73, CD90, CD105 and CD271 and (b) does not express detectable levels of CD14, CD34 and CD45.

The invention also provides:
a population comprising two or more progenitor cells of the invention;
a pharmaceutical composition comprising (a) a progenitor cell of the invention or a population of the invention and (b) a pharmaceutically acceptable carrier or diluent;
a method of producing a population the invention, comprising (a) culturing mononuclear cells (MCs) under conditions which induce the MCs to differentiate into progenitor cells of mesodermal lineage and (b) harvesting and culturing those progenitor cells which have an expression pattern of the invention and thereby producing a population of the invention;
a method of repairing a damaged tissue in a patient, comprising administering to the patient a population of the invention, wherein the population comprises a therapeutically effective number of cells, and thereby repairing the damaged tissue in the patient; and
a population of the invention for use in repairing a damaged tissue in a patient.

DETAILED DESCRIPTION OF THE INVENTION

Figure 1:
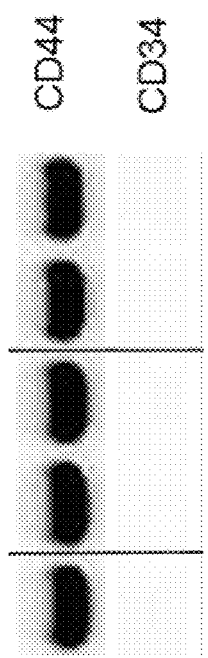
FIG. 1 shows an RT-PCR gel confirming the presence of CD44 and the absence of CD34 in the PMLs of the invention.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a cell" includes "cells", reference to "a tissue" includes two or more such tissues, reference to "a patient" includes two or more such patients, and the like.

All publications, patents and patent applications cited herein, whether supra or infra, are hereby incorporated by reference in their entirety.

PMLs of the Invention

The present invention provides a progenitor cell of mesodermal lineage (PML). The PML expresses detectable levels of CD29, CD44, CD73, CD90, CD105 and CD271, but does not express detectable levels of CD14, CD34 and CD45.

The PMLs of the invention have numerous advantages. The key advantages will be summarized here. However, further advantages will become apparent from the discussion below.

The PMLs of the invention may advantageously be used to repair damaged tissues in patients. The PMLs are capable of efficiently migrating (or homing) to a damaged tissue and exerting anti-inflammatory effects in the tissue. This is discussed in more detail below. One of the most important abilities of the PMLs is to migrate (or home) to injured sites, which involves chemotaxis. This is based on chemokine-signalling and utilises mechanisms such as rolling, adhesion and transmigration. The anti-inflammatory effects of the PMLs promote survival, repair and regeneration of the neighbouring cells in the damaged tissue. The cells are also able to exert paracrine effects such as the secretion of angiogenic, chemotactic and anti-apoptotic factors.

As discussed in more detail below, the PMLs are produced from mononuclear cells (MCs), such as peripheral MCs, taken from a human individual. Since the PMLs are produced from MCs, they may be produced easily (such as from peripheral blood) and may be autologous for the patient to be treated and thereby avoid the risk of immunological rejection by the patient.

It is possible, in principle, to produce an unlimited number of PMLs from a single individual, since various samples of MCs (i.e. various samples of blood) may be obtained. It is certainly possible to produce very large numbers of PMLs from a single individual. The PMLs of the invention can therefore be made in large numbers.

The PMLs of the invention are produced in clinically relevant conditions, for instance in the absence of trace amounts of endotoxins and other environmental contaminants, as well as animal products such as fetal calf serum. This makes the PMLs of the invention particularly suitable for administration to patients.

Since the PMLs of the invention are produced from MCs, they are substantially homologous and may be autologous. They also avoid donor-to-donor variation, which frequently occurs with mesenchymal stem cells (MSCs). Numerous populations of PMLs of the invention can be produced from a single sample taken from the patient before any other therapy, such as chemotherapy or radiotherapy, has begun. Therefore, the PMLs of the invention can avoid any of the detrimental effects of those treatments.

The PMLs of the invention can be made quickly. PMLs can be produced from MCs in less than 30 days, such as in about 22 days.

The production of PMLs from MCs avoids the moral and ethical implications involved with using mesenchymal stem cells (MSCs) derived from human embryonic stem cells (hESCs).

The PMLs of the invention are typically produced from human MCs. The PMLs of the invention are therefore typically human.

The PMLs of the invention can be identified as progenitor cells of mesodermal lineage using standard methods known in the art, including expression of lineage restricted markers, structural and functional characteristics. The PMLs will express detectable levels of cell surface markers known to be characteristic of progenitor cells of mesodermal lineage. In particular, in addition to the markers discussed in more detail below, the PMLs may express $\alpha$-smooth muscle actin, collagen type I $\alpha$-chain, GATA6, Mohawk, and vimentin (Sagi B et al Stem Cells Dev. 2012 Mar. 20; 21(5):814-28).

The PMLs of the invention are capable of successfully completing differentiation assays in vitro to confirm that they are of mesodermal lineage. Such assays include, but are not limited to, adipogenic differentiation assays, osteogenic differentiation assays and neurogenic differentiation assays (Zaim M et al Ann Hematol. 2012 August; 91(8):1175-86).

The PMLs of the invention are not stem cells. In particular, they are not mesenchymal stem cells (MSCs). They are terminally differentiated. Although they can be forced under the right conditions in vitro to differentiating, for instance into cartilage or bone cells, they do not differentiate in vivo. The PMLs of the invention have their effects by migrating to the damaged tissue and exerting paracrine signalling in the damaged tissue. In particular, the PMLs are preferably capable of inducing anti-flammatory effects in the damaged tissue. This is discussed in more detail below.

The PMLs of the invention are typically characterised by a spindle-shaped morphology. The PMLs are typically fibroblast-like, i.e. they have a small cell body with a few cell processes that are long and thin. The cells are typically from about 10 to about 20 µm in diameter.

The PMLs of the invention are distinguished from known PMLs via their marker expression pattern. The PMLs of the invention express detectable levels of CD29, CD44, CD73, CD90, CD105 and CD271. The PMLs of the invention may overexpress one or more of, such as all of, CD29, CD44, CD73, CD90, CD105 and CD271. The PMLs of the invention overexpress one or more of CD29, CD44, CD73, CD90, CD105 and CD271 if they express more than other PMLs and/or MSCs. The PMLs of the invention do not express detectable levels of CD14, CD34 and CD45.

CD29 (Beta 4 integrin) is an integrin unit associated with very late antigen receptors. It is known to conjoin with alpha-3 subunit to create an $\alpha 3\beta 1$ complex that reacts with netrin-1 and reelin.

CD44 is a cell-surface glycoprotein involved in cell-cell interactions, cell adhesion and migration. In humans, the CD44 antigen is encoded by the CD44 gene on Chromosome 11.

CD73, also known as ecto-5'-nucleotidase (ecto-5'-NT, EC 3.1.3.5), is a glycosylphosphatidylinositol-linked 70-kDa cell surface ectoenzyme found in many types of human and mouse cancers.

CD90 (or Thy-1) is a 25-37 kDa heavily N-glycosylated, glycophosphatidylinositol (GPI) anchored conserved cell surface protein with a single V-like immunoglobulin domain. It was originally discovered as a thymocyte antigen.

CD105 (or Endoglin) is a type I membrane glycoprotein located on cell surfaces and is part of the TGF beta receptor complex.

CD271, also known as low affinity nerve growth factor receptor (LNGFR) or p75NTR, belongs to the low affinity neurotrophin receptor and tumor necrosis factor receptor superfamily.

CD14 is a component of the innate immune system and exists in two forms. It is either anchored into the membrane by a glycosylphosphatidylinositol tail (mCD14) or it appears in a soluble form (sCD14). Soluble CD14 either appears after shedding of mCD14 (48 kDa) or is directly secreted from intracellular vesicles (56 kDa).

CD34 is a cell surface glycoprotein and functions as a cell-cell adhesion factor. For instance, it mediates the attachment of stem cells to bone marrow extracellular matrix or directly to stromal cells.

CD45 is a protein tyrosine phosphatase (PTP) located in hematopoietic cells except ethrocytes and platelets. CD45 is also called the common leukocyte antigen, T220 and B220 in mice. The protein tyrosine kinases constitute a family of receptor-like and cytoplasmic inducing enzymes that catalyze the dephosphorylation of phosphotyrosine residues and are characterized by homologous catalytic domains.

Standard methods known in the art may be used to determine the detectable expression, low expression or lack thereof of the various markers discussed above (and below). Suitable methods include, but are not limited to, immunocytochemistry, immunoassays, flow cytometry, such as fluorescence activated cells sorting (FACS), and polymerase chain reaction (PCR), such as reverse transcription PCR (RT-PCR). Suitable immunoassays include, but are not limited to, Western blotting, enzyme-linked immunoassays (ELISA), enzyme-linked immunosorbent spot assays (ELISPOT assays), enzyme multiplied immunoassay techniques, radioallergosorbent (RAST) tests, radioimmunoassays, radiobinding assays and immunofluorescence. Western blotting, ELISAs and RT-PCR are all quantitative and so can be used to measure the level of expression of the various markers if present. The use of FACS is disclosed in the Example. Antibodies and fluorescently-labelled antibodies for all of the various markers discussed herein are commercially-available.

The PMLs of the invention are preferably capable of migrating to a specific damaged tissue in a patient. In other words, when the cells are administered to a patient having a damaged tissue, the cells are capable of migrating (or homing) to the damaged tissue. This is advantageous because it means that the cells can be infused via standard routes, for instance intravenously, and will then target the site of damage. The cells do not have to be delivered to the damaged tissue. The damage may be due to injury or disease as discussed in more detail below.

The ability of the PMLs of the invention to migrate to damaged tissue may be measured using standard assays known in the art. Suitable methods include, but are not limited to, genomic reverse transcription polymerase chain reaction (RT-PCR with or without reporter genes) and labelling techniques.

RT-PCR is the most straightforward and simple means to trace the PMLs of the invention within a patient. A transduced transgene or individual donor markers can be used for this purpose and transplanted cell-specific signals have been obtained in several patient studies. The results are generally semi-quantitative.

Alternatively, the PMLs of the invention may be stained with a dye of interest, such as a fluorescent dye, and may be monitored in the patient via the signal from the dye. A specific method of such labelling is disclosed in the Example.

Migration (or homing) is typically determined by measuring the number of cells that arrive at the damaged tissue. It may also be measured indirectly by observing the numbers of cells that have accumulated in the lungs (rather than the damaged tissue).

The PMLs of the invention which are capable of migrating to a specific, damaged tissue in a patient preferably (a) express detectable levels of, or overexpress, C—X—C chemokine receptor type 1 (CXCR1) and/or (b) express detectable levels of, or overexpress, CXCR2. The PMLs of the invention more preferably express detectable levels of, or overexpress, CXCR1 and CXCR2. Damaged tissues release a variety of soluble inflammatory factors, such as macrophage migration inhibitory factor (MIF) and interleukin-8, and these factors may attract the PMLs of the invention (and other inflammatory cells) to the damaged tissue though binding to binding CXCR1 and/or CXCR2.

The PMLs of the invention overexpress CXCR1 and/or CXCR2 if they produce more CXCR1 and/or CXCR2 that other PMLs and/or MSCs. The expression of CXCR1 and/or CXCR2 may be measured as discussed above. The retinal-homing cells of the invention do not express detectable levels of CXCR1 and CXCR2. This is discussed in more detail below.

The specific, damaged tissue to which the PMLs of the invention are capable of migrating is preferably cardiac tissue, retinal tissue or bone tissue. The retinal tissue is preferably the macula.

If the specific, damaged tissue is heart tissue or bone tissue, the PMLs of the invention preferably express detectable levels of, or overexpress, C—X—C chemokine receptor type 4 (CXCR4). The PMLs of the invention overexpress CXCR4 if they express more CXCR4 that other PMLs and/or MSCs. If the specific, damaged tissue is heart tissue or bone tissue, the PMLs of the invention more preferably express detectable levels of, or overexpress, (a) CXCR1 and CXCR4; (b) CXCR2 and CXCR4; or (c) CXCR1, CXCR2 and CXCR4. The expression of CXCR4 may be measured as discussed above.

Damaged heart tissue releases inflammatory chemokines and cytokines, such as stromal cell-derived factor-1 (SDF-1), interleukin-8 (IL-8), tumor necrosis factor-alpha (TNF-alpha), granulocyte-colony-stimulating factor (G-CSF), vascular endothelial growth factor (VEGF) and hepatocyte growth factor (HGF). In addition, myocardial infarct increases the levels of VEGF and erythropoietin (EPO). CXCR4 binds to its ligand SDF-1 and so PMLs of the invention expressing CXCR4 will migrate towards the gradient of SDF-1 generated by the damaged heart tissue. Other damaged tissues, such as bone, also release SDF-1.

If the specific, damaged tissue is retinal tissue, such as the macula, the PMLs of the invention preferably express detectable levels of CXCR4, vascular endothelial growth factor (VEGF), transforming growth factor beta 1 (TGF-beta 1), insulin-like growth factor-1 (IGF-1), fibroblast growth factor (FGF), tumour necrosis factor alpha (TNF-alpha), interferon gamma (IFN-gamma), interleukin-1 alpha (IL-1 alpha), CXCL12, CD109, CD119, nuclear factor kappa-light-chain-enhancer of activated B cells (NFkappa B), CD140a, CD140b, CD221, CD222, CD304, CD309 and CD325. The retinal-homing PMLs of the invention preferably overexpress one or more of, or even all of, these factors. The PMLs overexpress these factors if they express more of the factors than other PMLs and/or MSCs. Quantitative assays for cell markers are described above.

Retinal-homing PMLs of the invention preferably also express detectable levels of pigment epithelium derived factor (PEDF) or overexpress PEDF. The detectable expression of these markers may be measured as discussed above. The PMLs of the invention overexpress PEDF if they express more PEDF than other PMLs and/or mesenchymal stem cells (MSCs).

If the specific, damaged tissue is bone tissue, the PMLs of the invention preferably express detectable levels of TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type 1 (CCR1), IGF-1 receptor (IGF-1R), hepatocyte growth factor receptor (HGFR), CXCL12 and NFkappaB. The bone-homing PMLs of the invention preferably overexpress one or more of, or even all of, these factors. The PMLs overexpress these factors if they express more of the factors than other PMLs and/or MSCs. The detectable expression of these markers may be measured as discussed above.

The PMLs of the invention are preferably capable of having anti-inflammatory effects in a damaged tissue of a patient. The ability of the PMLs of the invention to have anti-inflammatory effects may also be measured using standard assays known in the art. Suitable methods include, but are not limited to, enzyme-linked immunosorbent assays (ELISAs) for the secretion of cytokines, enhanced mixed leukocyte reactions and up-regulation of co-stimulatory molecules and maturation markers, measured by flow cytometry. Specific methods that may be used are disclosed in the Example. The cytokines measured are typically interleukins, such as interleukin-8 (IL-8), selectins, adhesion molecules, such as Intercellular Adhesion Molecule-1 (ICAM-1), and chemoattractant proteins, such as monocyte chemotactic protein-1 (MCP-1) and tumour necrosis factor alpha (TNF-alpha). Assays for these cytokines are commercially-available.

Anti-inflammatory PMLs preferably express detectable levels of CD120a (tumour-necrosis factor (TNF)-alpha Receptor 1), CD120b (TNF-alpha Receptor 2), CD50 (Intercellular Adhesion Molecule-3, ICAM-3), CD54 (ICAM-1), CD58 (Lymphocyte function-associated antigen-1, LFA-1), CD62E (E-selectin), CD62L (L-selectin), CD62P (P-selectin), CD106 (Vascular cell adhesion protein, VCAM-1), CD102 (ICAM-2), CD166 (Activated leukocyte cell adhesion molecule), CD104 (Beta 4 integrin), CD123 (Interleukin-3 Receptor), CD124 (Interleukin-4 Receptor), CD126 (Interleukin-6 Receptor), CD127 (Interleukin-7 Receptor) and fibroblast growth factor receptor (FGFR). Anti-inflammatory PMLs preferably overexpress one or more of, or even all of, these factors. The PMLs overexpress these factors if they express more of the one or more factors than other PMLs and/or MSCs. The detectable expression of these markers may be measured as discussed above.

The PMLs of the invention are more preferably capable of migrating to a damaged tissue in a patient and having anti-inflammatory effects in the damaged tissue. This allows the damage to be repaired effectively and reduces the number of cells that need to be administered.

The PMLs of the invention will express a variety of different other markers over and above those discussed above. Some of these will assist the PMLs will their ability to migrate to a damaged tissue and have anti-inflammatory effects once there. Any of the PMLs of the invention may further express detectable levels of one or more of (i) insulin-like growth factor-1 (IGF-1), (ii) IGF-1 receptor; (iii)C—C chemokine receptor type 1 (CCR1), (iv) stromal cell-derived factor-1 (SDF-1), (v) hypoxia-inducible factor-1 alpha (HIF-1 alpha), (vi) Akt1 and (vii) hepatocyte growth factor (HGF) and/or granulocyte colony-stimulating factor (G-CSF).

IGF-1 receptors promote migration capacity towards an IGF-1 gradient. One of the mechanisms by which IGF-1 increases migration is by up-regulating CXCR4 on the surface of the cells, which makes them more sensitive to SDF-1 signaling. This is discussed above.

CCR1 is the receptor for CCL7 (previously known as MCP3) increases homing and engraftment capacity of MSCs (and so would be expected to have the same effect for the PMLs of the invention) and can increase the capillary density in injured myocardium through paracrine signalling.

HIF-1 alpha activates pathways that increase oxygen delivery and promote adaptive pro-survival responses. Among the many target genes of HIF-1 alpha are erythropoietin (EPO), endothelin and VEGF (with its receptor Flk-1). PMLs that express or overexpress HIF-1alpha will have upregulated expression of paracrine stimuli of for example several vasculogenic growth factors that may promote a more therapeutic subtype. As described in more detail below, the PMLs of the invention can be preconditioned into a more therapeutic subtype by culturing them under hypoxic conditions (less than 20% oxygen), such as for example about 2% or about 0% oxygen.

Akt1 is an intracellular serine/threonine protein kinase that plays a key role in multiple cellular processes such as glucose metabolism, cell proliferation, apoptosis, transcription and cell migration. Overexpression of Akt1 has been shown to prevent rat MSCs from undergoing apoptosis and will have the same effect in the PMLs of the invention. Protection from apoptosis will enhance the therapeutic effect of the PMLs.

The overexpression of HGF by MSCs has been shown to prevent post-ischemic heart failure by inhibition of apoptosis via calcineurin-mediated pathway and angiogenesis. HGF and G-CSF exhibit synergistic effects in this regard. MSCs that have a high expression of HGF and its receptor c-met also have an increased migratory capacity into the damaged tissue, achieved through hormonal, paracrine and autocrine signaling. The same will be true for the PMLs of the invention expressing HGF and/or G-CSF.

The PMLs may overexpress one or more of (i) to (vii) defined above. The PMLs of the invention overexpress one or more of (i) to (vii) if they express more than other PMLs and/or than mesenchymal stem cells (MSCs). Quantitative assays for cell markers are described above. The detectable expression of these markers and their level of expression may be measured as discussed above.

Any of the PMLs of the invention may express detectable levels of one or more of (i) vascular endothelial growth factor (VEGF), (ii) transforming growth factor beta (TGF-beta), (iii) insulin-like growth factor-1 (IGF-1), (iv) fibroblast growth factor (FGF), (v) tumour necrosis factor alpha (TNF-alpha), (vi) interferon gamma (IFN-gamma) and (vii) interleukin-1 alpha (IL-1 alpha). Conditioned medium from cells overexpressing VEGF has been shown to alleviate heart failure in a hamster model. Hence, the PMLs of the invention which express or overexpress VEGF will have the same effect of damaged cardiac tissue.

The PMLs may overexpress one or more of (i) to (vii). The PMLs of the invention overexpress one or more of (i) to (vii) if they express more than other PMLs and/or than mesenchymal stem cells (MSCs). Quantitative assays for cell markers are described above. The detectable expression of these markers and their level of expression may be measured as discussed above.

In both sets of definitions of (i) to (vii) given above, any combination of one or more of (i) to (vii) may be expressed or overexpressed. For instance, for each definition of (i) to (vii), the PMLs may express detectable levels of, or overexpress, (i); (ii); (iii); (iv); (v); (vi); (vii); (i) and (ii); (i) and (iii); (i) and (iv); (i) and (v); (i) and (vi); (i) and (vii); (ii) and (iii); (ii) and (iv); (ii) and (v); (ii) and (vi); (ii) and (vii); (iii) and (iv); (iii) and (v); (iii) and (vi); (iii) and (vii); (iv) and (v); (iv) and (vi); (iv) and (vii); (v) and (vi); (v) and (vii); (vi) and (vii); (i), (ii) and (iii); (i), (ii) and (iv); (i), (ii) and (v); (i), (ii) and (vi); (i), (ii) and (vii); (i,), (iii) and (iv); (i), (iii) and (v); (i), (iii) and (vi); (i), (iii) and (vii); (i), (iv) and (v); (i), (iv) and (vi); (i), (iv) and (vii); (i), (v) and (vi); (i), (v) and (vii); (i), (vi) and (vii); (ii), (iii) and (iv); (ii), (iii) and (v); (ii), (iii) and (vi); (ii), (iii) and (vii); (ii), (iv) and (v); (ii), (iv) and (vi); (ii), (iv) and (vii); (ii), (v) and (vi); (ii), (v) and (vii); (ii), (vi) and (vii); (iii), (iv) and (v); (iii), (iv) and (vi); (iii), (iv) and (vii); (iii), (v) and (vi); (iii), (v) and (vii); (iii), (vi) and (vii); (iv), (v) and (vi); (iv), (v) and (vii); (iv), (vi) and (vii); (v), (vi) and (vii); (i), (ii), (iii) and (iv); (i), (ii), (iii) and (v); (i), (ii), (iii) and (vi); (i), (ii), (iii) and (vii); (i), (ii), (iv) and (v); (i), (ii), (iv) and (vi); (i), (ii), (iv) and (vii); (i), (ii), (v) and (vi); (i), (ii), (v) and (vii); (i), (ii), (vi) and (vii); (i), (iii), (iv) and (v); (i), (iii), (iv) and (vi); (i), (iii), (iv) and (vii); (i), (iii), (v) and (vi); (i), (iii), (v) and (vii); (i), (iii), (vi) and (vii); (i), (iv), (v) and (vi); (i), (iv), (v) and (vii); (i), (iv), (vi) and (vii); (i), (v), (vi) and (vii); (ii), (iii), (iv) and (v); (ii), (iii), (iv) and (vi); (ii), (iii), (iv) and (vii); (ii), (iii), (v) and (vi); (ii), (iii), (v) and (vii); (ii), (iii), (vi) and (vii); (ii), (iv), (v) and (vi); (ii), (iv), (v) and (vii); (ii), (iv), (vi) and (vii); (ii), (v), (vi) and (vii); (iii), (iv), (v) and (vi); (iii), (iv), (v) and (vii); (iii), (iv), (vi) and (vii); (iii), (v), (vi) and (vii); (iv), (v), (vi) and (vii); (i), (ii), (iii), (iv) and (v); (i), (ii), (iii), (iv) and (vi); (i), (ii), (iii), (iv) and (vii); (i), (ii), (iii), (v) and (vi); (i), (ii), (iii), (v) and (vii); (i), (ii), (iii), (vi) and (vii); (i), (ii), (iv), (v) and (vi); (i), (ii), (iv), (v) and (vii); (i), (ii), (iv), (vi) and (vii); (i), (ii), (v), (vi) and (vii); (i), (iii), (iv), (v) and (vi); (i), (iii), (iv), (v) and (vii); (i), (iii), (iv), (vi) and (vii); (i), (iii), (v), (vi) and (vii); (i), (iv), (v), (vi) and (vii); (ii), (iii), (iv), (v) and (vi); (ii), iii), (iv), (v) and (vii); (ii), (iii), (iv), (vi) and (vii); (ii), (iii), (v), (vi) and (vii); (ii), (iv), (v), (vi) and (vii); (iii), (iv), (v), (vi) and vii); (i), (ii), (iii), (iv), (v) and (vi); (i), (ii), (iii), (iv), (v) and (vii); (i), (ii), (iii), (iv), (vi) and (vii); (i), (ii), (iii), (v), (vi) and (vii); (i), (ii), (iv), (v), (vi) and (vii); (i), (iii), (iv), (v), (vi) and (vii); (ii), (iii), (iv), (v), (vi) and (vii); or (i), (ii), (iii), (iv), (v), (vi) and (vii). The combinations for each definition of (i) to (vii) are independently selectable from this list.

In addition to any of the markers discussed above, the PMLs of the invention preferably also express detectable levels of, or overexpress, LIF and/or platelet-derived growth factor (PDGF) receptors. The PDGF receptors are preferably PDGF-A receptors and/or PSDGF-B receptors. MSCs that have high expression of these receptors can migrate effectively into areas in which platelets have been activated, such as wounds and thrombotic vessels. The same will be true of PMLs expressing or overexpressing the receptors.

The PMLs of the invention are preferably autologous. In other words, the cells are preferably derived from the patient into which the cells will be administered. Alternatively, the PMLs are preferably allogeneic. In other words, the cells are preferably derived from a patient that is immunologically compatible with the patient into which the cells will be administered.

A PML of the invention may be isolated, substantially isolated, purified or substantially purified. The PML is isolated or purified if it is completely free of any other components, such as culture medium, other cells of the invention or other cell types. The PML is substantially isolated if it is mixed with carriers or diluents, such as culture medium, which will not interfere with its intended use. Alternatively, the PML of the invention may be present in a growth matrix or immobilized on a surface as discussed below.

PMLs of the invention may be isolated using a variety of techniques including antibody-based techniques. Cells may be isolated using negative and positive selection techniques based on the binding of monoclonal antibodies to those surface markers which are present on the PML (see above). Hence, the PMLs may be separated using any antibody-based technique, including fluorescent activated cell sorting (FACS) and magnetic bead separation.

As discussed in more detail below, the PMLs may be treated ex vivo. Thus the cells may be loaded or transfected with a therapeutic or diagnostic agent and then used therapeutically in the methods of the invention.

Population of the Invention

The invention also provides a population of two or more PMLs of the invention. Any number of cells may be present in the population. The population of the invention preferably comprises at least about $5\times10^5$ PMLs of the invention. The population more preferably comprises at least about $1\times10^6$, at least about $2\times10^6$, at least about $5\times10^6$, at least about $1\times10^7$, at least about $2\times10^7$, at least about $5\times10^7$, at least about $1\times10^8$ or at least about $2\times10^8$ PMLs of the invention. In some instances, the population may comprise at least about $1.0\times10^7$, at least about $1.0\times10^8$, at least about $1.0\times10^9$, at least about $1.0\times10^{10}$, at least about $1.0\times10^{11}$ or at about least $1.0\times10^{12}$ PMLs of the invention or even more.

The populations of the invention are advantageous for therapy as discussed below. This ability to produce populations comprising large numbers of PMLs of the invention is one of the key advantages of the invention. The invention allows the treatment of patients with a population of cells of which most, if not all, migrate efficiently to the tissue of interest and have anti-inflammatory effects once there. This allows the use of a low cell-dose and avoids off-target side effects and volume-related side effects.

The population of the invention may comprise other cells in addition to the PMLs of the invention. However, at least 70% of the cells in the population are preferably PMLs of the invention. More preferably, at least about 75%, at least about 80%, at least about 85%, at least about 90%, at least about 97%, at least about 98% or at least about 99% of the cells in the population are PMLs of the invention.

The population of the invention is preferably homologous. In other words, all of the PMLs in the population are preferably genotypically and phenotypically identical. The population is preferably autologous or allogeneic as defined above.

However, the population can also be semi-allogeneic. Semi-allogeneic populations are typically produced from mononuclear cells from two or more patients that are immunologically compatible with the patient into which the population will be administered. In other words, all of the cells in the population are preferably genetically identical or sufficiently genetically identical that the population is immunologically compatible with the patient into which the population will be administered. Since the PMLs of the invention may be derived from a patient, they may be autologous with the patient to be treated (i.e. genetically identical with the patient or sufficiently genetically identical that they are compatible for administration to the patient).

The population of the invention may be isolated, substantially isolated, purified or substantially purified. A population is isolated or purified if it is completely free of any other components, such as culture medium and other cells. A population is substantially isolated if it is mixed with carriers or diluents, such as culture medium, which will not interfere with its intended use. Other carriers and diluents are discussed in more detail below. A substantially isolated or substantially purified population does not comprise cells other than the PMLs of the invention. In some embodiments, the population of the invention may be present in a growth matrix or immobilized on a surface as discussed below.

The population is typically cultured in vitro. Techniques for culturing cells are well known to a person skilled in the art. The cells are may be cultured under standard conditions of 37° C., 5% $CO_2$ in medium without serum. The cells are preferably cultured under low oxygen conditions as discussed in more detail below. The cells may be cultured in any suitable flask or vessel, including wells of a flat plate such as a standard 6 well plate. Such plates are commercially available from Fisher scientific, VWR suppliers, Nunc, Starstedt or Falcon. The wells typically have a capacity of from about 1 ml to about 4 ml.

The flask, vessel or wells within which the population is contained or cultured may be modified to facilitate handling of the PMLs. For instance, the flask, vessel or wells may be modified to facilitate culture of the cells, for instance by including a growth matrix. The flask, vessel or wells may be modified to allow attachment of the PMLs or to allow immobilization of the PMLs onto a surface. One or more surfaces may be coated with extracellular matrix proteins such as laminin or collagen or any other capture molecules that bind to the cells and immobilize or capture them on the surface(s).

The population may be modified ex vivo using any of the techniques described herein. For instance, the population may be transfected or loaded with therapeutic or diagnostics agents. The population may then be used in the methods of treatment discussed in more detail below.

Method of Producing a PML of the Invention

The invention also provides a method for producing a population of the invention, i.e. a population of two or more PMLs of the invention. The method involves culturing mononuclear cells (MCs) under conditions which induce the MCs to differentiate into PMLs. The method then involves harvesting and culturing the PMLs which:

(a) express detectable levels of CD29, CD44, CD73, CD90, CD105 and CD271 and do not express detectable levels of CD14, CD34 and CD45;

(b) express detectable levels of CD29, CD44, CD73, CD90, CD105, CD271 and CXCR1 and do not express detectable levels of CD14, CD34 and CD45;

(c) express detectable levels of CD29, CD44, CD73, CD90, CD105, CD271 and CXCR2 and do not express detectable levels of CD14, CD34 and CD45;

(d) express detectable levels of CD29, CD44, CD73, CD90, CD105, CD271, CXCR1 and CXCR2 and do not express detectable levels of CD14, CD34 and CD45;

(e) express detectable levels of CD29, CD44, CD73, CD90, CD105, CD271, CXCR1 and CXCR4 and do not express detectable levels of CD14, CD34 and CD45 (these cells are heart-homing and bone-homing PMLs);

(f) express detectable levels of CD29, CD44, CD73, CD90, CD105, CD271, CXCR2 and CXCR4 and do not express detectable levels of CD14, CD34 and CD45 (these cells are heart-homing and bone-homing PMLs);

(g) express detectable levels of CD29, CD44, CD73, CD90, CD105, CD271, CXCR1, CXCR2 and CXCR4 and do not express detectable levels of CD14, CD34 and CD45 (these cells are heart-homing and bone-homing PMLs);

(h) express detectable levels of CD29, CD44, CD73, CD90, CD105, CD271, CXCR4, vascular endothelial growth factor (VEGF), transforming growth factor beta 1 (TGF-beta 1), insulin-like growth factor-1 (IGF-1), fibroblast growth factor (FGF), tumour necrosis factor alpha (TNF-alpha), interferon gamma (IFN-gamma), interleukin-1 alpha (IL-1 alpha), CXCL12, CD109, CD119, nuclear factor kappa-light-chain-enhancer of activated B cells (NFkappa B), CD140a, CD140b, CD221, CD222, CD304, CD309 and CD325 and do not express detectable levels of CD14, CD34 and CD45 (these cells are retinal-homing PMLs); or (i) express detectable levels of CD29, CD44, CD73, CD90, CD105, CD271, TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type 1 (CCR1), IGF-1 receptor (IGF-1R), hepatocyte growth factor receptor (HGFR), CXCL12 and NFkappaB and do not express detectable levels of CD14, CD34 and CD45 (these cells are bone-homing PMLs).

The harvested cells may overexpress any of the factors as described above with reference to the cells of the invention. In addition to any one of (a) to (i) above, the method preferably involves harvesting and culturing PMLs which:

(j) express detectable levels of CD120a (tumour-necrosis factor (TNF)-alpha Receptor 1), CD120b (TNF-alpha Receptor 2), CD50 (Intercellular Adhesion Molecule-3, ICAM-3), CD54 (ICAM-1), CD58 (Lymphocyte function-associated antigen-1, LFA-1), CD62E (E-selectin), CD62L (L-selectin), CD62P (P-selectin), CD106 (Vascular cell adhesion protein, VCAM-1), CD102 (ICAM-2), CD166 (Activated leukocyte cell adhesion molecule), CD104 (Beta 4 integrin), CD123 (Interleukin-3 Receptor), CD124 (Interleukin-4 Receptor), CD126 (Interleukin-6 Receptor), CD127 (Interleukin-7 Receptor) and fibroblast growth factor receptor (FGFR);

(k) express detectable levels of one or more of (i) insulin-like growth factor-1 (IGF-1), (ii) IGF-1 receptor; (iii) C—C chemokine receptor type 1 (CCR1), (iv) stromal cell-derived factor-1 (SDF-1), (v) hypoxia-inducible factor-1 alpha (HIF-1 alpha), (vi) Akt1 and (vii) hepatocyte growth factor (HGF) and/or granulocyte colony-stimulating factor (G-CSF);

(l) overexpress one or more of (i) to (vii) in (k);

(m) express detectable levels of one or more of (i) vascular endothelial growth factor (VEGF), (ii) transforming growth factor beta (TGF-beta), (iii) insulin-like growth factor-1 (IGF-1), (iv) fibroblast growth factor (FGF), (v) tumour necrosis factor alpha (TNF-alpha), (vi) interferon gamma (IFN-gamma) and (vii) interleukin-1 alpha (IL-1 alpha)

(n) overexpress one or more of (i) to (vii) in (m).

Mononuclear cells (MCs) and methods of isolating them are known in the art. The MCs may be primary MCs isolated from bone marrow. The MCs are preferably peripheral blood MCs (PBMCs), such as lymphocytes, monocytes and/or macrophages. PBMCs can be isolated from blood using a hydrophilic polysaccharide, such as Ficoll®. For instance, PBMCs may be isolated from blood using Ficoll-Paque® (a commercially-available density medium) as disclosed in the Example.

Before they are cultured, the MCs may be exposed to a mesenchymal stem cell enrichment cocktail. The cocktail preferably comprises antibodies that recognise CD3, CD14, CD19, CD38, CD66b (which are present on unwanted cells) and a component of red blood cells. Such a cocktail cross links unwanted cells with red blood cells forming immunorosettes which may be removed from the wanted MCs. A preferred cocktail is RosetteSep®.

Conditions suitable for inducing MCs to differentiate into mesenchymal cells (tissue mainly derived from the mesoderm) are known in the art. For instance, suitable conditions are disclosed in Capelli, C., et al. (Human platelet lysate allows expansion and clinical grade production of mesenchymal stromal cells from small samples of bone marrow aspirates or marrow filter washouts. Bone Marrow Transplantation, 2007. 40: p. 785-791). These conditions may also be used to induce MCs to differentiate into PMLs in accordance with the invention.

The method preferably comprises culturing MCs with plasma lysate to induce the MCs to differentiate into PMLs. Platelet lysate refers to the combination of natural growth factors contained in platelets that has been released through lysing those platelets. Lysis can be accomplished through chemical means (i.e. $CaCl_2$)), osmotic means (use of distilled $H_2O$) or through freezing/thawing procedures. Platelet lysate can be derived from whole blood as described in U.S. Pat. No. 5,198,357. Platelet lysate is preferably prepared as described in the Example. The plasma lysate is preferably human plasma lysate.

In a preferred embodiment, step (a) of the method of the invention comprises culturing MCs in a medium comprising platelet lysate for sufficient time to induce the MCs to differentiate into progenitor cells of mesodermal lineage. The sufficient time is typically from about 15 to about 25 days, preferably about 22 days. The medium preferably comprises about 20% or less platelet lysate by volume, such as about 15% or less by volume or about 10% or less by volume. The medium preferably comprises from about 5% to about 20% of platelet lysate by volume, such as from about 10% to about 15% by volume. The medium preferably comprises about 10% of platelet lysate by volume.

In another preferred embodiment, step (a) of the method of the invention comprises exposing MCs to a mesenchymal enrichment cocktail and then culturing the MCs in a medium comprising platelet lysate for sufficient time to induce the MCs to differentiate into progenitor cells of mesodermal lineage. The sufficient time is typically from about 15 to about 25 days, preferably about 22 days.

In step (a), the medium is preferably Minimum Essential Medium (MEM). MEM is commercially available from various sources including Sigma-Aldrich. The medium preferably further comprises one or more of heparin, L-glutamine and penicillin/streptavidin (P/S). The L-glutamine may be replaced with GlutaMAX® (which is commercially-available from Life Technologies).

As discussed above, some of the PMLs of the invention express detectable levels of CXCR4. Expression of CXCR4 is cytokine-dependent and is increased when cells are exposed to stem cell factor (SCF), interleukin-6 (IL-6), Flt-3 ligand, hepatocyte growth factor (HGF) and IL-3. The medium may comprise one or more of (i) SCF, (ii) IL-6, (iii) Flt-3 ligand, (iv) hepatocyte growth factor and (v) IL-3, such as (i); (ii); (iii); (iv); (v); (i) and (ii); (i) and (iii); (i) and (iv); (i) and (v); (ii) and (iii); (ii) and (iv); (ii) and (v); (iii) and (iv); (iii) and (v); (iv) and (v); (i), (ii) and (iii); (i), (ii) and (iv); (i), (ii) and (v); (i), (iii) and (iv); (i), (iii) and (v); (i), (iv) and (v); (ii), (iii) and (iv); (ii), (iii) and (v); (ii), (iv) and (v); (iii), (iv) and (v); or (i), (ii), (iii), (iv) and (v). Any of (i) to (v) may be present at from about from about 10 to about about 150 ng/ml.

Step (a) preferably comprises culturing the MCs under conditions which allow the PMLs to adhere. Suitable conditions are discussed in more detail above.

In step (a), the MCs are preferably cultured under low oxygen conditions. The MCs are preferably cultured at less than about 20% oxygen ($O_2$), such as less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2% or less than about 1% oxygen ($O_2$). The MCs are preferably cultured at from about 0% to about 19% $O_2$, such as from about 1% to about 15% $O_2$, from about 2% to about 10% $O_2$ or from about 5% to about 8% $O_2$. The MCs are most preferably cultured at about 0% $O_2$. The figures for % oxygen (or % $O_2$) quoted above relate to % by volume of oxygen in the gas supplied to the cells during culture, for instance by the cell incubator. It is possible that some oxygen may leak into the incubator or enter when the door is opened.

In step (a), the MCs are most preferably cultured in the presence of platelet lysate and under low oxygen conditions. This combination mimics the natural conditions in the damaged tissue and so result in healthier and more therapeutically potent cells. Conventional cell culture is performed in 20% or 21% oxygen (approximately the atmospheric content) but there is no place in the human body that has this oxygen level. The epithelial cells in the lungs would "see" this oxygen level, but once the oxygen is dissolved and leaves the lungs, it decreases to around 17%. From there, it decreases even further to about 1-2% in the majority of the tissues, but being as low as 0.1% in avascular tissues such as the cartilage in the joints.

In step (b), the method further comprises harvesting and culturing PMLs which have the necessary marker expression pattern as discussed above. The PMLs having the necessary marker expression pattern may be harvested using any antibody-based technique, including fluorescent activated cell sorting (FACS) and magnetic bead separation. FACS is preferred.

Any of the methods for culturing PMLs disclosed in relation to step (a) equally apply to step (b). In particular, the cells are cultured in step (b) in the presence of platelet lysate and under low oxygen conditions as discussed above in relation to step (a).

As will be clear from the discussion above, the method of the invention is carried out in clinically relevant conditions, i.e. in the absence of trace amounts of endotoxins and other environmental contaminants, such as lipopolysaccharides, lipopeptides and peptidoglycans, etc. This makes the PMLs of the invention particularly suitable for administration to patients.

The MCs are preferably obtained from a patient or an allogeneic donor. The invention also provides a method for producing a population of the invention that is suitable for administration to a patient, wherein the method comprises culturing MCs obtained from the patient under conditions which induce the MCs to differentiate into progenitor cells of mesodermal lineage and (b) harvesting and culturing those progenitor cells which have an expression pattern as defined above and thereby producing a population of the invention that is suitable for administration to the patient. The population will be autologous with the patient and therefore will not be rejected upon implantation. The invention also provides a population of the invention that is suitable for administration to a patient and is produced in this manner.

Alternatively, the invention provides a method for producing a population of the invention that is suitable for administration to a patient, wherein the method comprises culturing MCs obtained from a different patient that is immunologically compatible with the patient into which the cells will be administered under conditions which induce the MCs to differentiate into progenitor cells of mesodermal lineage and (b) harvesting and culturing those progenitor cells which have an expression pattern as defined above and thereby producing a population of the invention that is suitable for administration to the patient. The population will be allogeneic with the patient and therefore will reduce the chance of rejection upon implantation. The invention also provides a population of the invention that is suitable for administration to a patient and is produced in this manner.

Medicaments, Methods and Therapeutic Use

The PMLs of the invention may be used in a method of therapy of the human or animal body. Thus the invention provides a PML of the invention or a population of the invention for use in a method of treatment of the human or animal body by therapy. In particular, the invention concerns using the PMLs of the invention to repair a damaged tissue in a patient. The invention also concerns using the PMLs of the invention to treat a cardiac injury or disease, age-related macular degeneration or a bone injury or disease in the patient.

The invention provides a method of repairing a damaged tissue in a patient, comprising administering to the patient a population of the invention, wherein the population comprises a therapeutically effective number of cells, and thereby treating the damaged tissue in the patient. The invention also provides a population of the invention for use in repairing a damaged tissue in the patient. The invention also provides use of a population of the invention in the manufacture of a medicament for repairing a damaged tissue in a patient.

The tissue is preferably derived from the mesoderm. The tissue is more preferably cardiac tissue, retinal tissue or bone tissue.

The damage to the tissue may be caused by injury or disease. The injury or disease is preferably a cardiac injury or disease, age-related macular degeneration (AMD) or a bone injury or disease in a patient. The invention therefore provides a method of treating a cardiac injury or disease, age-related macular degeneration or a bone injury or disease in a patient, comprising administering to the patient a population of the invention, wherein the population comprises a therapeutically effective number of cells, and thereby treating the cardiac injury or disease, age-related macular degeneration or bone injury or disease in the patient. The invention also provides a population of the invention for use in treating a cardiac injury or disease, age-related macular degeneration or a bone injury or disease in a patient. The invention also provides use of a population of the invention in the manufacture of a medicament for treating a cardiac injury or disease, age-related macular degeneration or a bone injury or disease in a patient.

The cardiac injury or disease is preferably selected from myocardial infarct (MI), left ventricular hypertrophy, right ventricular hypertrophy, emboli, heart failure, congenital heart deficit, heart valve disease, arrhythmia and myocarditis.

MI increases the levels of VEGF and EPO released by the myocardium. Furthermore, MI is associated with an inflammatory reaction and infarcted tissue also releases macrophage migration inhibitory factor (MIF), interleukin (IL-6) and KC/Gro-alpha. CCL7 (previously known as MCP3), CXCL1, CXCL2 are significantly upregulated in the heart following myocardial infarct (MI) and might be implicated in regulating engraftment and homing of MSCs to infarcted myocardium.

In a myocardial infarct mice model, IL-8 was shown to highly up-regulate gene expression primarily in the first 2 days post-MI. Remarkably, the increased IL-8 expression was located predominantly in the infarcted area and the border zone, and only to a far lesser degree in the spared myocardium. By activating CXCR2, MIF displays chemokine-like functions and acts as a major regulator of inflammatory cell recruitment and atherogenesis.

The AMD may be dry AMD or wet AMD. Dry AMD results from atrophy of the retinal pigment epithelial layer below the retina which causes vision loss through loss of photoreceptors (rods and cones) in the central part of the eye. Wet AMD causes vision loss due to abnormal blood vessel growth (choroidal neovascularization) in the choriocapillaris, through Bruch's membrane, ultimately leading to blood and protein leakage below the macula. Wet AMD is associated with a decrease in the levels of pigment epithelium derived factor (PEDF) in the macula. The PMLs used in the treatment of wet AMD preferably express detectable levels of PEDF or overexpress PEDF.

The bone disease or injury is preferably selected from fracture, Salter-Harris fracture, greenstick fracture, bone spur, craniosynostosis, Coffin-Lowry syndrome, fibrodysplasia ossificans progressive, fibrous dysplasia, Fong Disease (or Nail-patella syndrome), hypophosphatasia, Klippel-Feil syndrome, Metabolic Bone Disease, Nail-patella syndrome, osteoarthritis, osteitis deformans (or Paget's disease of bone), osteitis fibrosa cystica (or Osteitis fibrosa or Von Recklinghausen's disease of bone), osteitis pubis, condensing osteitis (or osteitis condensans), osteitis condensans ilii, osteochondritis dissecans, osteogenesis imperfecta, osteomalacia, osteomyelitis, osteopenia, osteopetrosis, osteoporosis, osteonecrosis, porotic hyperostosis, primary hyperparathyroidism, renal osteodystrophy, bone cancer, a bone lesion associated with metastatic cancer, Gorham Stout disease, primary hyperparathyroidism, periodontal disease, and aseptic loosening of joint replacements. The bone cancer can be Ewing sarcoma, multiple myeloma, osteosarcoma (giant tumour of the bone), osteochondroma or osteoclastoma. The metastatic cancer that results in a bone lesion can be breast cancer, prostate cancer, kidney cancer, lung cancer and/or adult T-cell leukemia.

If the damaged tissue is cardiac tissue or bone tissue, the PMLs in the population preferably express detectable levels of CD29, CD44, CD73, CD90, CD105, CD271, CXCR1, CXCR2 and CXCR4 and do not express detectable levels of CD14, CD34 and CD45. If the damaged tissue is bone tissue, the PMLs in the population more preferably express detectable levels of CD29, CD44, CD73, CD90, CD105, CD271, TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type 1 (CCR1), IGF-1 receptor (IGF-1R), hepatocyte growth factor receptor (HGFR), CXCL12 and NFkappaB and do not express detectable levels of CD14, CD34 and CD45.

If the damaged tissue is retinal tissue, the PMLs in the population preferably express detectable levels of CD29, CD44, CD73, CD90, CD105, CD271, CXCR4, vascular endothelial growth factor (VEGF), transforming growth factor beta 1 (TGF-beta 1), insulin-like growth factor-1 (IGF-1), fibroblast growth factor (FGF), tumour necrosis factor alpha (TNF-alpha), interferon gamma (IFN-gamma), interleukin-1 alpha (IL-1 alpha), CXCL12, CD109, CD119, nuclear factor kappa-light-chain-enhancer of activated B cells (NFkappa B), CD140a, CD140b, CD221, CD222, CD304, CD309 and CD325 and do not express detectable levels of CD14, CD34 and CD45.

In all instances, the PMLs of the invention are preferably derived from the patient or an allogeneic donor. Deriving the PMLs of the invention from the patient should ensure that the PMLs are themselves not rejected by the patient's immune system. Any difference between the donor and recipient will ultimately cause clearance of the PMLs, but not before they have repaired at least a part of the damaged tissue.

The invention concerns administering to the patient a therapeutically effective number of PMLs of the invention to the patient. A therapeutically effective number is a number which ameliorates one or more symptoms of the damage, disease or injury. A therapeutically effective number is preferably a number which repairs the damaged tissue or treats the disease or injury. Suitable numbers are discussed in more detail below.

The PMLs of the invention may be administered to any suitable patient. The patient is generally a human patient. The patient may be an infant, a juvenile or an adult. The patient may be known to have a damaged tissue or is suspected of having a damaged tissue. The patient may be susceptible to, or at risk from, the relevant disease or injury. For instance, the patient may be genetically predisposed to heart failure.

The invention may be used in combination with other means of, and substances for, repairing damaged tissue or providing pain relief. In some cases, the PMLs of the invention may be administered simultaneously, sequentially or separately with other substances which are intended for repairing the damaged tissue or for providing pain relief. The PMLs may be used in combination with existing treatments for damaged tissue and may, for example, be simply mixed with such treatments. Thus the invention may be used to increase the efficacy of existing treatments of damaged tissue.

The invention preferably concerns the use of PMLs loaded or transfected with a therapeutic and/or diagnostic agent. A therapeutic agent may help to repair the damaged tissue. A diagnostic agent, such as a fluorescent molecule, may help to identify the location of the PMLs in the patient. The PMLs may be loaded or transfected using any method known in the art. The loading of PMLs may be performed in vitro or ex vivo. In each case, the PMLs may simply be in contact with the agent in culture. Alternatively, the PMLs may be loaded with an agent using delivery vehicle, such as liposomes. Such vehicles are known in the art.

The transfection of PMLs may be performed in vitro or ex vivo. Alternatively, stable transfection may be perfomed at the MC stage allowing PMLs expressing the transgene to be differentiated from them. The PMLs are transfected with a nucleic acid encoding the agent. For instance, viral particles or other vectors encoding the agent may be employed. Methods for doing this are known in the art.

The nucleic acid gives rise to expression of the agent in the PMLs. The nucleic acid molecule will preferably comprise a promoter which is operably linked to the sequences encoding the agent and which is active in the PMLs or which can be induced in the PMLs.

In a particularly preferred embodiment, the nucleic acid encoding the agent may be delivered via a viral particle. The viral particle may comprise a targeting molecule to ensure efficient transfection. The targeting molecule will typically be provided wholly or partly on the surface of the virus in order for the molecule to be able to target the virus to the PMLs.

Any suitable virus may be used in such embodiments. The virus may, for example, be a retrovirus, a lentivirus, an adenovirus, an adeno-associated virus, a vaccinia virus or a herpes simplex virus. In a particularly preferred embodiment the virus may be a lentivirus. The lentivirus may be a modified HIV virus suitable for use in delivering genes. The lentivirus may be a SIV, FIV, or equine infectious anemia virus (EQIA) based vector. The virus may be a moloney murine leukaemia virus (MMLV). The viruses used in the invention are preferably replication deficient.

Viral particles do not have to be used. Any vector capable of transfecting the PMLs of the invention may be used, such as conventional plasmid DNA or RNA transfection.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectAmine, fugene and transfectam.

The cell may be loaded or tranfected under suitable conditions. The cell and agent or vector may, for example, be contacted for between five minutes and ten days, preferably from an hour to five days, more preferably from five hours to two days and even more preferably from twelve hours to one day.

The invention also provides PMLs which have been loaded or transfected with an agent as discussed above. Such PMLs may be used in the therapeutic embodiments of the invention.

In some embodiments, MCs may be recovered from a patient, converted into PMLs using the invention, loaded or transfected in vitro and then returned to the same patient. In such instances, the PMLs employed in the invention, will be autologous cells and fully matched with the patient. In a preferred case, the cells employed in the invention are recovered from a patient and utilised ex vivo and subsequently returned to the same patient.

Pharmaceutical Compositions and Administration

The invention additionally provides a pharmaceutical composition comprising (a) a PML of the invention or a population of the invention and (b) a pharmaceutically acceptable carrier or diluent. The composition may comprise any of the PMLs or populations mentioned herein and, in some embodiments, the nucleic acid molecules, vectors, or viruses described herein. The invention provides a method of repairing a damaged tissue in a patient comprising administering to the patient an effective amount of a pharmaceutical composition of the invention. Any of the therapeutic embodiments discussed above equally apply to this embodiment.

The various compositions of the invention may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, $19^{th}$ Edition, Mack Publishing Company, Eastern Pennsylvania, USA.

The cells may be administered by any route. Suitable routes include, but are not limited to, intravenous, intramuscular, intraperitoneal or other appropriate administration routes. If the damaged tissue is retinal tissue, the cells may be administered to the eye. If the damaged tissue is cardiac tissue, the cells may be administered via an endomyocardial, epimyocardial, intraventicular, intracoronary, retrograde coronary sinus, intra-arterial, intra-pericardial or intravenous route. If the damaged tissue is bone, the cells may be administered via an intraosseous route or to the site of the injury, such as a fracture, or disease. The cells are preferably administered intravenously.

Compositions may be prepared together with a physiologically acceptable carrier or diluent. Typically, such compositions are prepared as liquid suspensions of cells. The cells may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions of the invention may contain minor amounts of auxiliary substances such as wetting or emulsifying agents, pH buffering agents, and/or adjuvants which enhance effectiveness. The composition preferably comprises human serum albumin.

One suitable carrier or diluents is Plasma-Lyte A®. This is a sterile, nonpyrogenic isotonic solution for intravenous administration. Each 100 mL contains 526 mg of Sodium Chloride, USP (NaCl); 502 mg of Sodium Gluconate (C6H11NaO7); 368 mg of Sodium Acetate Trihydrate, USP (C2H3NaO2.3H2O); 37 mg of Potassium Chloride, USP (KCl); and 30 mg of Magnesium Chloride, USP (MgCl2.6H2O). It contains no antimicrobial agents. The pH is adjusted with sodium hydroxide. The pH is 7.4 (6.5 to 8.0).

The PMLs are administered in a manner compatible with the dosage formulation and in such amount will be therapeutically effective. The quantity to be administered depends on the subject to be treated, capacity of the subject's immune system and the degree repair desired. Precise amounts of PMLs required to be administered may depend on the judgement of the practitioner and may be peculiar to each subject.

Any suitable number of cells may be administered to a subject. For example, at least, or about, $0.5 \times 10^6$, $1.5 \times 10^6$, $4.0 \times 10^6$ or $5.0 \times 10^6$ cells per kg of patient may administered. For example, at least, or about, $10^5$, $10^6$, $10^7$, $10^8$, $10^9$ cells may be administered. As a guide, the number of cells of the invention to be administered may be from $10^5$ to $10^9$, preferably from $10^6$ to $10^8$. Typically, up to $2 \times 10^8$ PMLs are administered to each patient. Any of the specific numbers discussed above with reference to the populations of the invention may be administered. In such cases where cells are administered or present, culture medium may be present to facilitate the survival of the cells. In some cases the cells of the invention may be provided in frozen aliquots and substances such as DMSO may be present to facilitate survival during freezing. Such frozen cells will typically be thawed and then placed in a buffer or medium either for maintenance or for administration.

The following Example illustrates the invention.

EXAMPLE

Materials and Methods

Once blood was taken from patients, progenitor cells of mesodermal origin were prepared in a stem cell laboratory under hygienic conditions; open containers with cells or other material were handled under a laminar-flow hood. At each preparation step, samples were drawn and stem cell number and viability was determined.

Mononuclear cells were isolated from whole blood by Ficoll-Paque® 1.073 density centrifugation and were cultured in α-MEM-PL for 5 days. Adherent cells were harvested and their immunophenotypes were determined by immunofluorescence staining for a number of cellular markers (see below) by flow cytometric analysis. Appropriate isotype controls were used for each staining procedure.

Cell viability was assessed with 1% trypan blue solution. Cells will be enumerated by FACS (FACSCalibur, Beckton Dickinson). Cells were also tested for *mycoplasma*, sterility (assessed by gram stain), endotoxin, identity, purity, and viability and karyotyping to exclude chromosomal abnormalities.

The following summarises how the cells were actually derived.
1. 20 ml of peripheral blood was taken from the patient.
2. 11.5 ml of remaining blood was then passed through the Ficoll Paque® 1.073.
3. This was centrifuged to give mononuclear cells these were either then:
4a. Grown in culture for 8 days in 0% oxygen or
4b. Run through Rosette Separation and then grown in culture for 8 days in 0% oxygen.
5. Media was changed and cells were in culture for 14 days in 0% oxygen.
6. The cells were then harvested and then run through FACS. A variety of markers were investigated using RT-PCR and FACS analysis. The main markers investigated were CD14, CD29, CD34, CD44, CD45, CD73, CD90, CD105, CD271, CD181, CD182 and CD184.

The following is the working protocol that was used.
Platelet-Rich Plasma (PRP) Preparation
1. The blood sample was divided into two 15 ml Falcon tubes, >8 ml in each.
2. Centrifuged at 120×g, 15 min, no brake, room temperature (RT).
3. The platelet-rich plasma (PRP) supernatant was transferred to a new 15 ml Falcon tube.
4. The volume of the transferred PRP was noted.
5. The volume of PRP was replaced with Hank's Balanced Salt Solution (HBSS).

Culture Media Preparation
1. 0.3 ml PRP was transferred to an eppendorf tube for automatic haematology analysis using the Cell-Dyn instrument. The theoretical maximum number of platelets was calculated.

Theoretical maximum number of platelets=Platelet concentration×PRP volume
2. 0.25 ml PRP was transferred to an eppendorf tube for cryopreservation (−80° C.).
3. The remaining PRP was centrifuged at 1610×g, 10 min, RT, with brake.
4. The platelet free plasma (PFP) supernatant was removed into a separate falcon tube and the platelet pellet was re-suspended with a volume of PFP that gives a concentration of $1 \times 10^9$ cells/ml (using the theoretical max number of platelets—aim for $1.5 \times 10^9$ to achieve $1 \times 10^9$).
5. The remaining PFP was transferred into eppendorf tubes in 0.25 ml aliquots for cryopreservation (−80° C.).
6. The lid of the PRP falcon tube was wrapped in parafilm.
7. The falcon tube was submerged in liquid nitrogen for 5 mins.
8. The falcon tube was submerged in 37° C. water bath until thawed.
9. Steps 7 and 8 were repeated a further 3 times.
10. Culture media was made up by adding the PL at 10% to αMEM, 5 U/ml Heparin, 2 mM glutamax, 1% P/S (i.e. add 1.5 ml PL to 13.5 ml media).

MNC isolation
1. The diluted blood sample volume (16.5 ml) was combined into a new 50 ml Falcon tube.
2. The blood sample was further diluted 1:2 with HBSS to ~33 ml.
3. 15 ml of Ficoll-Paque PREMIUM 1.073 was added to two new 50 ml Falcon tubes.
4. The diluted blood sample was carefully layered on top of the Ficoll-Paque by tilting the tube and ejecting the sample slowly against the tube wall.
5. This was centrifuged at 400×g, 35 min, no brake, RT.
6. As much of the supernatant (the HBSS) as possible was disgarded without interrupting the cloudy mononuclear cell layer with the help of a soft Pasteur pipette.
7. The cloudy mononuclear cell layer that is resting on top of the clear Ficoll-Paque was aspirated to a new 50 ml tube, pooled!
8. The volume of transferred MNCs was noted by aspirating it into a 10 ml pipette.
9. Half of the volume was transferred to a new 50 ml tube.

10. The MNCs were diluted in both tubes with at least 3× the sample volume with HBSS, about 13 ml.
11. Both tubes were centrifuged at 500×g, 15 min, with brake, RT.
12. The supernatant was discarded.
13. One of the tubes was resuspended to approximately 1 million MNCs/ml, about 5 ml.

Rosette-Sep Enrichment
1. The second MNC pellet was resuspended with 660 μL whole blood from the initial 0.75 ml aliquot.
2. 33 μL Rosette-Sep was added and mixed by pipetting.
3. This was incubated for 20 minutes, room temperature.
4. The sample was diluted 1:2 by adding 700 μL HBSS, to a total sample volume of ~1.4 ml.
5. 1 ml of Ficoll-Paque was added to a new 15 ml Falcon tube.
6. The diluted blood sample was carefully layered on top of the Ficoll-Paque.
7. This was centrifuged at 400×g, 35 min, no brake, RT.
8. The supernatant was discarded by aspirating it with a 1 ml single-channel pipette.
9. The cloudy cell layer on top of the Ficoll was transferred to a new 15 ml Falcon tube.
10. The volume of enriched cells was noted and they were diluted with at least 3× the sample volume with HBSS, about 3 ml.
11. The cells were centrifuged at 500×g, 15 min, with brake, RT.
12. The supernatant was discarded.
13. The pellet was resuspended in 0.5 ml.

Cell culture
1. The cells were seeded at a seeding density of $1.0 \times 10^5$ cells into either autologous or allogeneic platelet lysate medium.
2. This was topped up with a suitable medium volume.
3. The cells were incubated in 37° C., 0% O2, 5% $CO_2$ for 8 days.
4. The media were changed on day 8 and the cells were incubated until day 14.
5. The colonies were picked and transferred to new culture vessels. Allogeneic platelet lysate medium were added.
6. The culturing and passaging of the cells was continued until approximately $5 \times 10^5$-$1 \times 10^6$ cells were obtained.
7. The cells were harvested and analysed by flow cytometry and, as necessary, the cells were cryopreserved.

Homing and Anti-Inflammatory Tests

The cells produced in accordance with the invention were tested for their ability to home to specific, damaged tissues in mice and induce anti-inflammatory effects once there. For homing, cells were labelled with fluorescent agent and their location in the mouse body determined using bioluminescence.

For anti-inflammatory effects, enzyme-linked immunosorbent assays (ELISAs) for various inflammatory markers, including interleukins (such as IL-8), selectins, adhesion molcules (such as ICAM-1) and chemoattractant proteins (such as MCP-1 and TNF-α), were performed.

Results

All Cells

All progenitor cells of mesodermal lineage produced in accordance with the invention expressed CD29, CD44, CD73, CD90, CD105 and CD271, but did not express CD14, CD34 and CD45. An exemplary RT-PCR gel showing the presence of CD44 and the absence of CD34 is shown in FIG. 1.

Figure 2:
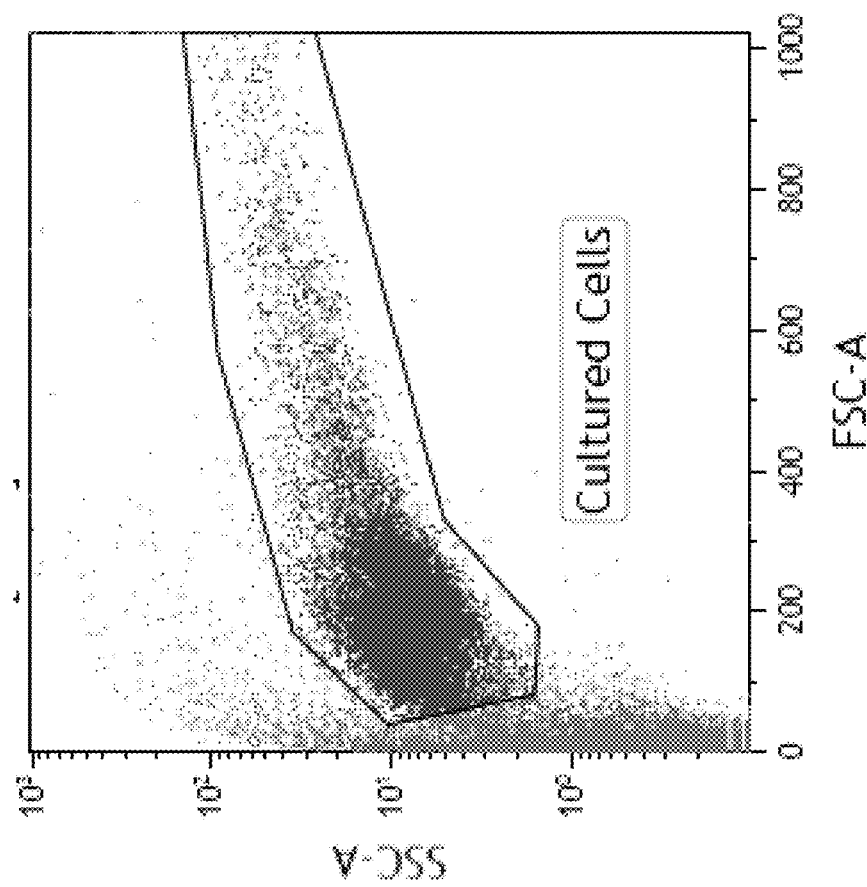
FIG. 2 shows the results of FACS analysis on the PMLs of the invention. This confirms that the cells are positive for at least CD73 and CD90 and negative for CD14, CD34 and CD45.
Figure 3:
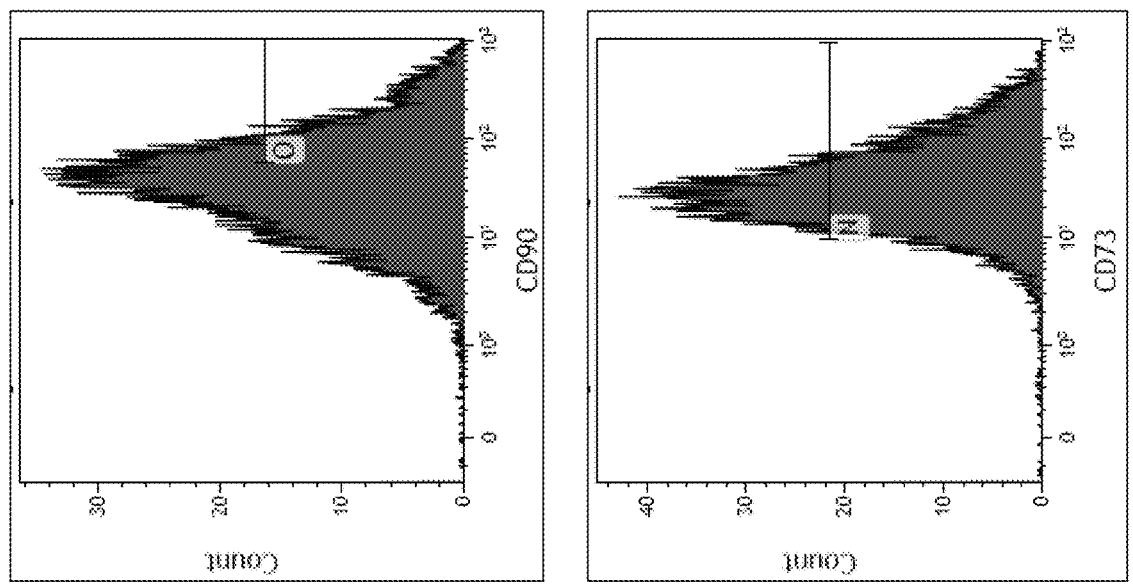
FIG. 3 shows further results from FACS analysis, namely the histograms for CD90 (top) and CD73 (bottom).
Figure 4A:
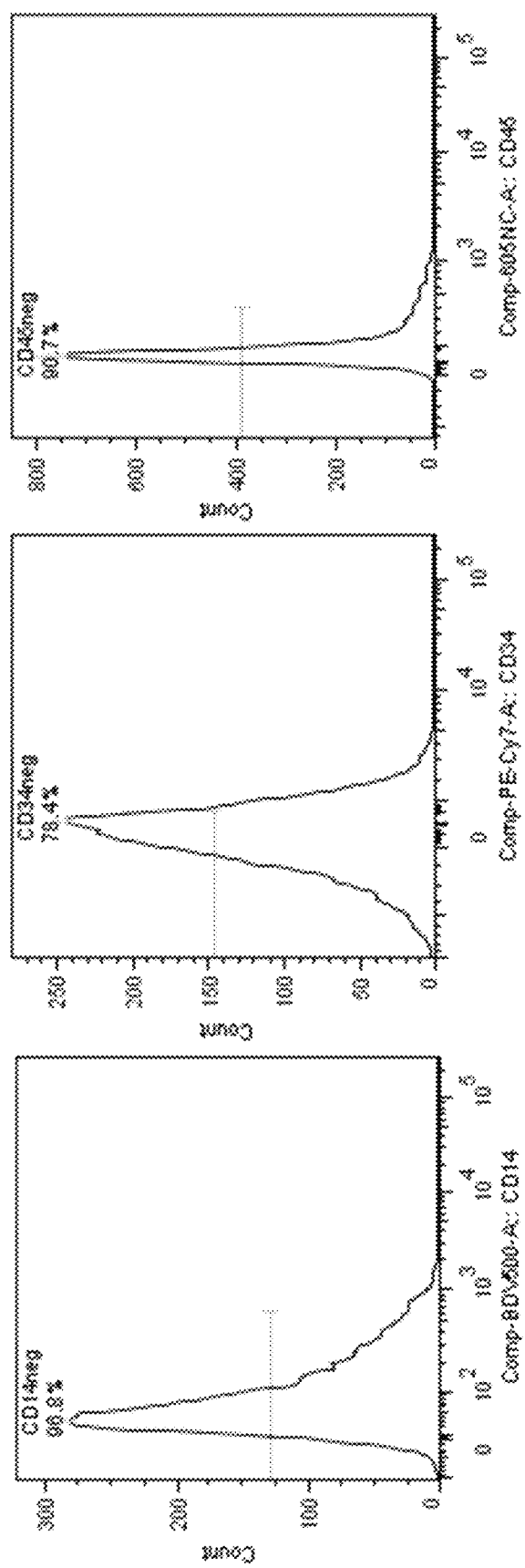
FIG. 4 shows FACS histograms for lack of CD14, CD34 and CD45 in stained (FIG. 4a) and unstained (FIG. 4b) cells.
Figure 4B:
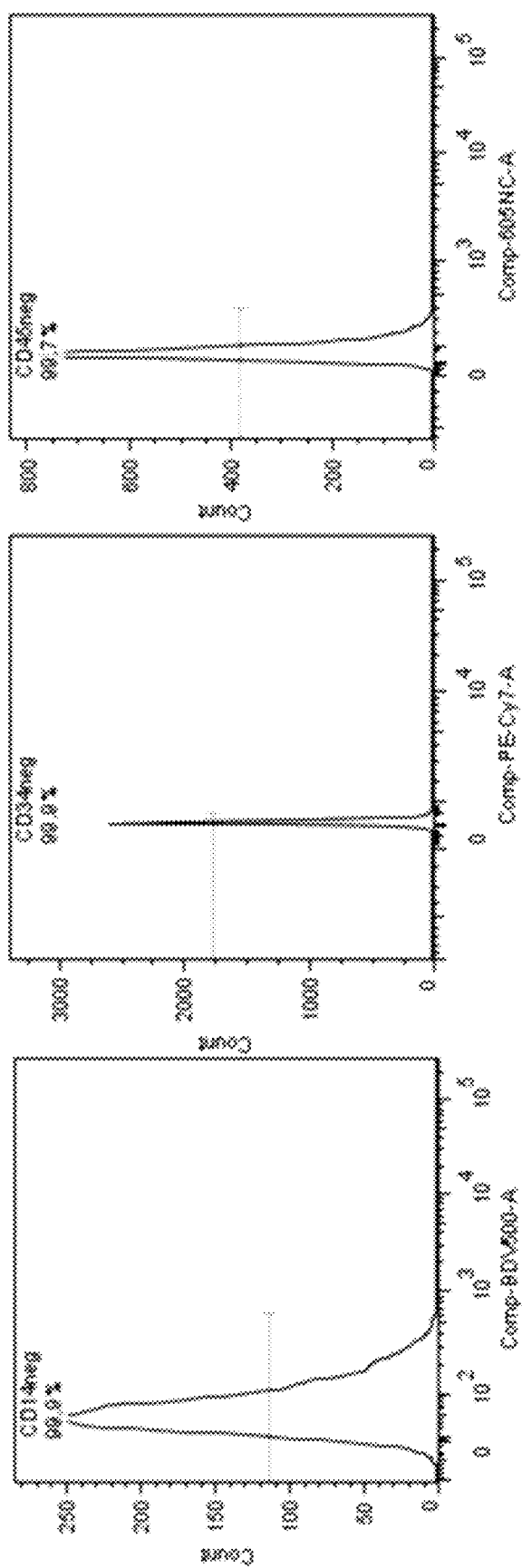

Exemplary sets of FACS results are shown in FIGS. 2 to 4. These confirms that the cells are cells are positive for at least CD73 and CD90 and negative for CD14, CD34 and CD45.

The cells are typically from 10 to 20 μm in diameter. The cells typically have a spindle-shaped morphology and are fibroblast like (i.e. they have a small cell body with a few cell processes that are long and thin).

Homing Cells

Cells capable of homing to specific damaged tissues were shown to express chemokine receptor types 1 and 2 (CXCR1 and CXCR2).

Cells capable of homing to damaged heart tissue and bone tissues were shown to express CXCR4.

Cells capable of homing to damaged retinal tissue were shown to express CXCR4, vascular endothelial growth factor (VEGF), transforming growth factor beta 1 (TGF-beta 1), insulin-like growth factor-1 (IGF-1), fibroblast growth factor (FGF), tumour necrosis factor alpha (TNF-alpha), interferon gamma (IFN-gamma), interleukin-1 alpha (IL-1 alpha), CXCL12, CD109, CD119, nuclear factor kappa-light-chain-enhancer of activated B cells (NFkappa B), CD140a, CD140b, CD221, CD222, CD304, CD309 and CD325.

Cells capable of homing to damaged bone tissue and the cell expresses detectable levels of TGF-beta 3, bone morphogenetic protein-6 (BMP-6), SOX-9, Collagen-2, CD117 (c-kit), chemokine (C—C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type 1 (CCR1), IGF-1 receptor (IGF-1R), hepatocyte growth factor receptor (HGFR), CXCL12 and NFkappaB.

Anti-Inflammatory Effects

The cells produced in accordance with the invention were shown to express the following anti-inflammatory markers: CD120a (tumour-necrosis factor (TNF)-alpha Receptor 1), CD120b (TNF-alpha Receptor 2), CD50 (Intercellular Adhesion Molecule-3, ICAM-3), CD54 (ICAM-1), CD58 (Lymphocyte function-associated antigen-1, LFA-1), CD62E (E-selectin), CD62L (L-selectin), CD62P (P-selectin), CD106 (Vascular cell adhesion protein, VCAM-1), CD102 (ICAM-2), CD166 (Activated leukocyte cell adhesion molecule), CD104 (Beta 4 integrin), CD123 (Interleukin-3 Receptor), CD124 (Interleukin-4 Receptor), CD126 (Interleukin-6 Receptor), CD127 (Interleukin-7 Receptor) and fibroblast growth factor receptor (FGFR).

The invention claimed is:

1. An isolated population of progenitor cells of mesodermal lineage, wherein the cells (a) express detectable levels of CD29, CD44, CD73, CD90, CD105, CD271, CD120a (tumour-necrosis factor (TNF)-alpha Receptor 1), CD120b (TNF-alpha Receptor 2), CD50 (Intercellular Adhesion Molecule-3, ICAM-3), CD54 (ICAM-1), CD58 (Lymphocyte function-associated antigen-1, LFA-1), CD62E (E-selectin), CD62L (L-selectin), CD62P (P-selectin), CD106 (Vascular cell adhesion protein, VCAM-1), CD102 (ICAM-2), CD166 (Activated leukocyte cell adhesion molecule), CD104 (Beta 4 integrin), CD123 (Interleukin-3 Receptor), CD124 (Interleukin-4 Receptor), CD126 (Interleukin-6 Receptor), CD127 (Interleukin-7 Receptor) and fibroblast growth factor receptor (FGFR) and (b) do not express detectable levels of CD14, CD34 and CD45, and wherein at least 80% of the population comprises the progenitor cells of mesodermal lineage.

2. The progenitor cell population according to claim 1, wherein the cell population is capable of migrating to a specific, damaged tissue in a patient.

3. The progenitor cell population according to claim 2, wherein the cell population expresses detectable levels of C—X—C chemokine receptor type 1 (CXCR1).

4. The progenitor cell population according to claim 2, wherein the cell population expresses detectable levels of C—X—C chemokine receptor type 2 (CXCR2).

5. The progenitor cell population according to claim 2, wherein the specific tissue is cardiac tissue, retinal tissue or bone tissue.

6. The progenitor cell population according to claim 5, wherein the specific tissue is heart tissue or bone tissue and the cell population expresses detectable levels of C—X—C chemokine receptor type 4 (CXCR4).

7. The progenitor cell population according to claim 5, wherein the specific tissue is retinal tissue and the cell population expresses detectable levels of CXCR4, vascular endothelial growth factor (VEGF), transforming growth factor beta 1 (TGF-beta 1), insulin-like growth factor-I (IGF-1), fibroblast growth factor (FGF), tumour necrosis factor alpha (TNF-alpha), interferon gamma (IFN-gamma), interleukin-1 alpha (IL-1 alpha), CXCLI2, CD109, CD119, nuclear factor kappa-light-chain-enhancer of activated B cells (NFkappa B), CD140a, CD140b, CD221, CD222, CD304, CD309 and CD325.

8. The progenitor cell population according to claim 5, wherein the specific tissue is bone tissue and the cell population expresses detectable levels of TGF-beta3, bone morphogenetic protein-6 (BMP-6), SOX-9, Collagen-2, CD117 (C-kit), chemokine (C-C motif) ligand 12 (CCL12), CCL7, interleukin-8 (IL-8), platelet-derived growth factor-A (PDGF-A), PDGF-B, PDGF-C, PDGF-D, macrophage migration inhibitory factor (MIF), IGF-1, hepatocyte growth factor (HGF), PDGF-Rα, PDGF-Rβ, CXCR4, C—C chemokine receptor type I (CCR1), IGF-1 receptor (IG1-1R), hepatocyte growth factor receptor (HGFR), CXCL12 and NFkappaB.

9. The progenitor cell population according to claim 1, wherein the cell population is capable of having anti-inflammatory effects in a damaged tissue in a patient.

10. The progenitor cell population according to claim 1, wherein the cell population expresses detectable levels of one or more of (i) insulin-like growth factor-1 (IGF-1), (ii) IGF-1 receptor; (iii)C—C chemokine receptor type 1 (CCR1), (iv) stromal cell-derived factor-I (SDF-1), (v) hypoxia-inducible factor-1 alpha (HIF-1 alpha), (vi) Akt1 and (vii) hepatocyte growth factor (HGF) and/or granulocyte colony-stimulating factor (G-CSF).

11. The progenitor cell population according to claim 10, wherein the cell population overexpresses one or more of (i) to (vii).

12. The progenitor cell population according to claim 1, wherein the cell population expresses detectable levels of one or more of (i) vascular endothelial growth factor (VEGF), (ii) transforming growth factor beta (TGF-beta), (iii) insulin-like growth factor-1 (IGF-1), (iv) fibroblast growth factor (FGF), (v) tumour necrosis factor alpha (TNF-alpha), (vi) interferon gamma (IFN-gamma) and (vii) interleukin-1 alpha (IL-1 alpha).

13. The progenitor cell population according to claim 12, wherein the cell population overexpresses one or more of (i) to (vii).

14. The progenitor cell population according to claim 1, wherein the cell population is autologous with reference to a patient into which the cell population will be administered.

15. The progenitor cell population according to claim 1, wherein the cell population is allogeneic with reference to a patient into which the cell population will be administered.

16. The progenitor cell population according to claim 1, wherein the population comprises at least about $5 \times 10^5$ cells.

17. A pharmaceutical composition comprising (a) a progenitor cell population according to claim 1 and (b) a pharmaceutically acceptable carrier or diluent.

18. The progenitor cell population according to claim 1, wherein the cell population is capable of migrating to and repairing damaged tissue.

19. The progenitor cell population according to claim 1, wherein at least 85% of the population comprises the progenitor cells of mesodermal lineage.

20. The progenitor cell population according to claim 1, wherein at least 90% of the population comprises the progenitor cells of mesodermal lineage.

21. The progenitor cell population according to claim 1, wherein at least 97% of the population comprises the progenitor cells of mesodermal lineage.

22. The progenitor cell population according to claim 1, wherein at least 98% of the population comprises the progenitor cells of mesodermal lineage.

23. The progenitor cell population according to claim 1, wherein at least 99% of the population comprises the progenitor cells of mesodermal lineage.

24. The progenitor cell population according to claim 1, wherein the population is produced by a method comprising culturing mononuclear cells and/or progenitor cells with platelet lysate, wherein the cells are cultured at about 0% oxygen for about 15 days to about 25 days.

* * * * *